United States Patent
Bowman et al.

(10) Patent No.: US 7,520,867 B2
(45) Date of Patent: Apr. 21, 2009

(54) SUBCUTANEOUS INFUSION SET

(75) Inventors: Leif N. Bowman, Stevenson Ranch, CA (US); Albert D. Candioty, Agoura Hills, CA (US); Milad T. Girgis, North Hills, CA (US); Thomas V. Rudolph, Canyon Country, CA (US); Frederick C. Houghton, Moorpark, CA (US); Jason Adams, Frisco, TX (US); Brian Highley, Keller, TX (US)

(73) Assignee: Medtronic Minimed, Inc., Northridge, CA (US)

( * ) Notice: Subject to any disclaimer, the term of this patent is extended or adjusted under 35 U.S.C. 154(b) by 2 days.

(21) Appl. No.: 10/705,686

(22) Filed: Nov. 10, 2003
(Under 37 CFR 1.47)

(65) Prior Publication Data
US 2005/0101910 A1 May 12, 2005

(51) Int. Cl.
*A61M 31/00* (2006.01)

(52) U.S. Cl. ............... 604/93.01; 604/174; 604/506

(58) Field of Classification Search .............. 604/93.01, 604/110, 122, 164, 165, 167, 174–175, 177, 604/180, 246–248, 264, 905, 164.01–164.13, 604/165.01–165.04, 167.01–167.06, 288.01–288.04, 604/288, 502, 506, 500; 128/912, DIG. 6, 128/DIG. 26
See application file for complete search history.

(56) References Cited

U.S. PATENT DOCUMENTS

| 4,601,708 | A | | 7/1986 | Jordan |
| 4,645,495 | A | * | 2/1987 | Vaillancourt ............... 604/180 |
| 4,685,903 | A | | 8/1987 | Cable et al. |
| 4,743,231 | A | * | 5/1988 | Kay et al. .................... 604/180 |
| 4,755,173 | A | * | 7/1988 | Konopka et al. ....... 604/167.02 |
| 4,787,891 | A | | 11/1988 | Levin et al. |
| 4,813,939 | A | * | 3/1989 | Marcus ....................... 604/177 |
| 4,955,861 | A | * | 9/1990 | Enegren et al. ............. 604/141 |
| 4,966,589 | A | | 10/1990 | Kaufman |
| 4,988,339 | A | | 1/1991 | Vadher |
| 4,994,042 | A | | 2/1991 | Vadher |
| 5,122,119 | A | | 6/1992 | Lucas |
| 5,147,375 | A | | 9/1992 | Sullivan |
| 5,176,662 | A | * | 1/1993 | Bartholomew et al. ....... 604/513 |
| 5,257,980 | A | * | 11/1993 | Van Antwerp et al. ...... 604/506 |
| 5,368,045 | A | | 11/1994 | Clement et al. |

(Continued)

FOREIGN PATENT DOCUMENTS

EP 1 421 968 A2 5/2004

OTHER PUBLICATIONS

PCT International Search Report/Written Opinion dated Apr. 13, 2006 for PCT/US2005/041006.

*Primary Examiner*—Nicholas D Lucchesi
*Assistant Examiner*—Theodore J Stigell
(74) *Attorney, Agent, or Firm*—Foley & Lardner LLP

(57) ABSTRACT

A subcutaneous infusion set. The subcutaneous infusion set may include a base for providing an infusion path; a cannula connected to and extending away from the base; a connector removably attachable to the base; and a tubing affixed to the connector. The connector may be limitedly rotatable on the base when the connector is removably attached to the base. Also, a contiguous pass for passing fluids may be formed from the tubing to the cannula when the connector is removably attached to the base.

40 Claims, 10 Drawing Sheets

U.S. PATENT DOCUMENTS

| | | | |
|---|---|---|---|
| 5,390,671 A | 2/1995 | Lord et al. | |
| 5,522,803 A * | 6/1996 | Teissen-Simony | 604/177 |
| 5,545,143 A * | 8/1996 | Fischell | 604/180 |
| 5,545,152 A | 8/1996 | Funderburk et al. | |
| 5,562,631 A | 10/1996 | Bogert | |
| 5,568,806 A | 10/1996 | Cheney, II et al. | |
| 5,584,813 A | 12/1996 | Livingston et al. | |
| 5,586,553 A | 12/1996 | Halili et al. | |
| 5,591,188 A | 1/1997 | Waisman | |
| 5,607,407 A * | 3/1997 | Tolkoff et al. | 604/523 |
| 5,779,665 A | 7/1998 | Mastrototaro et al. | |
| 5,851,197 A | 12/1998 | Marano et al. | |
| 5,868,711 A | 2/1999 | Kramer et al. | |
| 5,957,895 A | 9/1999 | Sage et al. | |
| 5,968,011 A * | 10/1999 | Larsen et al. | 604/288.02 |
| 5,980,506 A * | 11/1999 | Mathiasen | 604/535 |
| 6,017,328 A * | 1/2000 | Fischell et al. | 604/180 |
| 6,093,172 A | 7/2000 | Funderburk et al. | |
| 6,123,690 A * | 9/2000 | Mejslov | 604/533 |
| 6,290,677 B1 * | 9/2001 | Arai et al. | 604/183 |
| 6,293,925 B1 | 9/2001 | Safabash et al. | |
| 6,302,866 B1 * | 10/2001 | Marggi | 604/174 |
| 6,355,021 B1 * | 3/2002 | Nielsen et al. | 604/263 |
| 6,461,329 B1 * | 10/2002 | Van Antwerp et al. | 604/111 |
| 6,572,586 B1 * | 6/2003 | Wojcik | 604/165.01 |
| 6,579,265 B1 * | 6/2003 | Kihara et al. | 604/174 |
| 6,579,267 B2 * | 6/2003 | Lynch et al. | 604/174 |
| 6,685,674 B2 * | 2/2004 | Douglas et al. | 604/167.05 |
| 6,736,797 B1 * | 5/2004 | Larsen et al. | 604/167.05 |
| 6,923,791 B2 * | 8/2005 | Douglas | 604/167.05 |
| 2002/0022855 A1 | 2/2002 | Bobroff et al. | |
| 2002/0072720 A1 | 6/2002 | Hague et al. | |
| 2002/0119711 A1 | 8/2002 | Van Antwerp et al. | |
| 2004/0138620 A1 | 7/2004 | Douglas et al. | |
| 2005/0020972 A1 * | 1/2005 | Horisberger et al. | 604/93.01 |
| 2005/0101910 A1 | 5/2005 | Bowman et al. | |
| 2005/0101933 A1 * | 5/2005 | Marrs et al. | 604/506 |
| 2005/0107746 A1 | 5/2005 | Pajunk et al. | |
| 2005/0113761 A1 | 5/2005 | Faust et al. | |

* cited by examiner

SUBCUTANEOUS INFUSION SET

BACKGROUND

1. Field of the Invention

The present invention relates to infusion sets and, in particular, to disposable infusion sets having a soft catheter which is inserted into the skin for the subcutaneous delivery of a fluid to a patient.

2. Description of Related Art

Subcutaneous infusion sets are generally used by patients for delivering a fluid or drug to a subcutaneous location in the patient. While most infusion sets include a delivery tube that may be connected to an infusion pump or other fluid or drug delivering device, the delivery tubes of prior art infusion sets have been disadvantageous to patients for a variety of reasons.

Some infusion sets of the prior art include a base portion disposed on the skin of the patient and a connector portion that attaches to the base portion. A delivery tube may be attached to the connector portion. Thus, when the connector portion is attached to the base portion, the delivery tube may be connected to an infusion pump or other device for fluid delivery. However, if the connector portion of the infusion set is rigidly attached to the base portion, the delivery tube may be oriented in a position that is undesirable or impractical for the patient. If the delivery tube is in a position that is undesirable or impractical for the patient, the patient is resigned to removing the base portion from the patient's skin and inserting a new infusion set base, since the old one cannot be safely reused. It is not normally possible to re-orient the base portion because re-orienting the base portion typically includes re-inserting a needle into the skin. Also, re-orienting the base portion can be discomforting, painful or could lead to infection and thus is undesirable for the patient.

Some infusion sets of the prior art have been proposed so that the connector portion and, thus, the delivery tube, may rotate freely about the base portion. While infusion sets of this type have allowed patients to freely position the orientation of the delivery tubes, freely rotating infusion sets have other disadvantages. Generally, too much movement of the delivery tube is undesirable. For example, because the delivery tube is typically delivering a fluid or some type of drug or infusant to a patient, it is necessary that the fluid path remain unobstructed. If the delivery tube is permitted to rotate freely around the base portion of the infusion set, the delivery tube may be subject to entanglement, twisting, kinking or the like, interrupting the infusion process.

What is needed is a subcutaneous infusion set that gives the patient the flexibility to adjust the location of the delivery tube without the disadvantages associated with delivery tubes that are free to rotate completely around the infusion site.

SUMMARY

It is an object of an embodiment of the present invention to provide an improved infusion set, which obviates for practical purposes, the above mentioned limitations.

According to an embodiment of the present invention, an infusion set may include a base for providing an infusion path; a cannula connected to and extending away from the base; a connector removably attachable to the base; and a tubing affixed to the connector. The connector may be limitedly rotatable to less than 360 degrees on the base when the connector is removably attached to the base. Also, a contiguous passage for passing fluids may be formed from the tubing to the cannula when the connector is removably attached to the base.

The base may include at least one barrier extending away from a surface of the base and the connector may include at least one stop extending away from a surface of the connector. The at least one barrier may be disposed on the base so that it restricts the movement of the at least one stop when the connector is rotated about the base. The connector may be limited to a rotation of 60 degrees, 90 degrees or 120 degrees when the connector may be removably attached to the base.

The infusion set may also include a hub removably affixable to the base; a needle attached to the hub, the needle being removably insertable into the cannula; and a cover for covering the needle. An adhesive pad may be affixed to the base. The cannula may extend through the adhesive pad.

According to another embodiment of the present invention, a method for using an infusion set may include positioning a base on an infusion site; positioning a connector onto the base, the connector including a delivery tubing; and adjusting a position of the delivery tubing. Adjusting the position of the delivery tubing may be limited to a range of less than 360 degrees. Also, adjusting the position of the delivery tubing may be limited to a range of 120 degrees, 90 degrees, 60 degrees or 30 degrees.

According to another embodiment of the present invention, a subcutaneous infusion set may include a base portion having a receiving area; a cannula affixed to the base portion; a connector portion for removable attachment to the base, the connector being received in the receiving area of the base portion; and a tubing affixed to the connector portion. An angular movement of the connector portion may be restricted by the base portion to less than 360 degrees and a fluid may pass from the tubing to the cannula when the connector is attached to the base.

The base portion may include at least one first member extending away from a surface of the base portion. The connector portion may include at least one second member extending away from a surface of the connector portion.

The at least one first member may be disposed on the base portion so that it restricts the movement of the at least one second member when the connector portion is rotated about the base portion. The connector portion may be limited to a rotation of 60 degrees, 90 degrees or 120 degrees when the connector is removably attached to the base portion.

The infusion set may also include a hub removably affixable to the base portion; a needle attached to the hub and a cover for covering the needle. The needle may be removably insertable into the cannula. Also, an adhesive pad may be affixed to the base. The cannula may extend through the adhesive pad.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 6 shows another side view of a connector according to an embodiment of the present invention.

DETAILED DESCRIPTION

Figure 1:
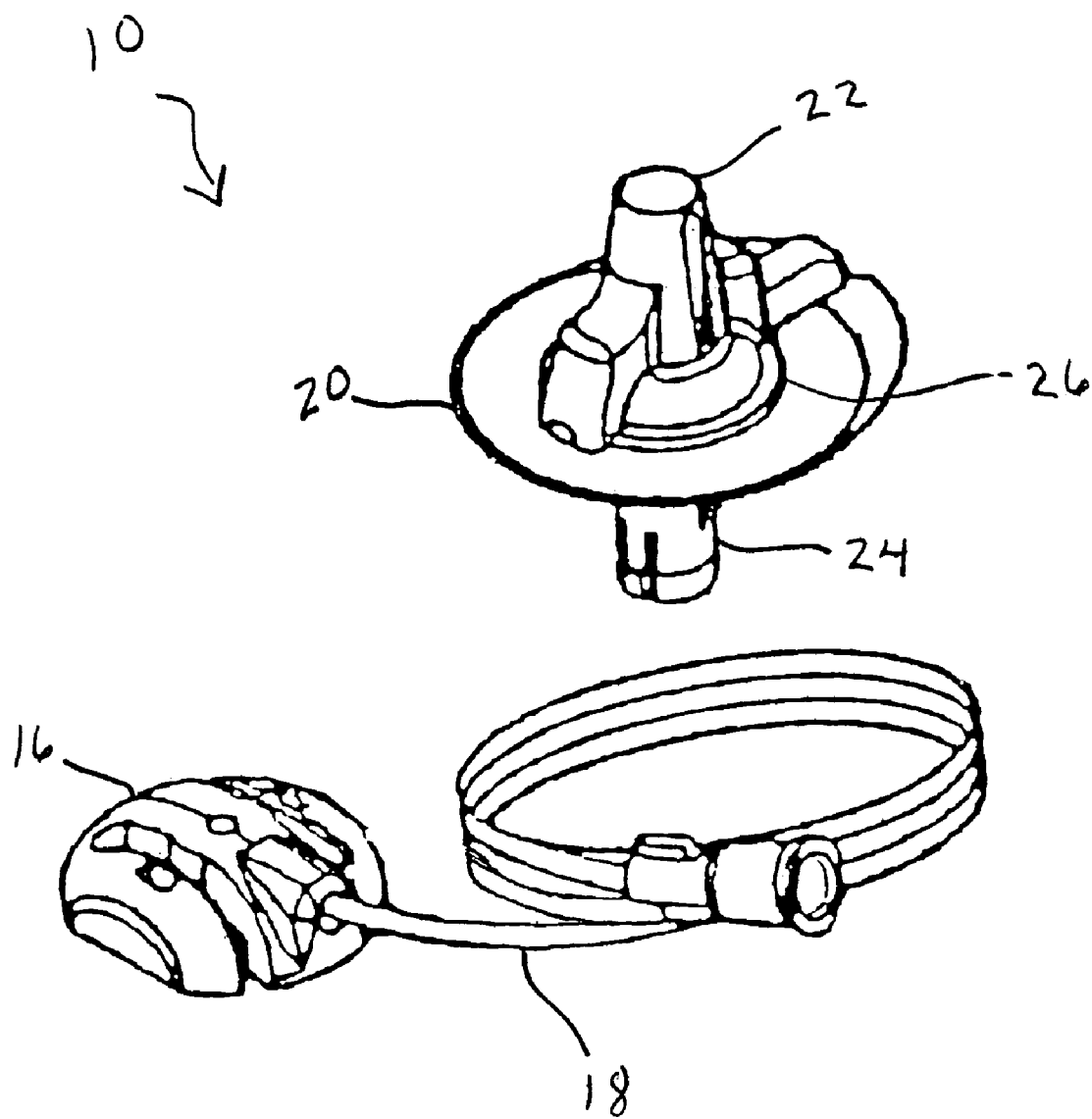
FIG. 1 shows a perspective view of a subcutaneous infusion set according to an embodiment of the present invention.

The following detailed description is of the best presently contemplated mode of implementing the invention. This description is not to be taken in a limiting sense, but is made merely for the purpose of illustrating the general principles of the invention. The scope of the invention is best defined by the appended claims.

As shown in the drawings for purposes of illustration, the invention is embodied in an infusion set for infusion of a liquid, such as medication, chemicals, enzymes, antigens, hormones, vitamins or the like, into a body of a user. Particular embodiments are directed towards use in humans; however, in alternative embodiments, the external infusion devices may be used in animals.

FIG. 1 shows a perspective view of a subcutaneous infusion set 10 according to an embodiment of the present invention. The subcutaneous infusion set 10 shown in FIG. 1 may include, without limitation, a holding pad 20, a needle hub 22, a needle guard 24, a base 26, a connector 16 and a delivery tubing 18. As will be explained in greater detail below, the subcutaneous infusion set 10 may be used by placing the holding pad 20 on the skin of a patient, removing the needle hub 22 and attaching the connector 16 to the base 26. Fluids may be delivered to a patient through the delivery tubing 18.

The subcutaneous infusion set 10 may be used in a variety of applications. For example, the subcutaneous infusion set 10 may be used for delivering a fluid to a subcutaneous location in a patient. According to an embodiment of the present invention, the subcutaneous infusion set 10 may be used to deliver insulin to a subcutaneous location in a diabetic patient.

Figure 2:
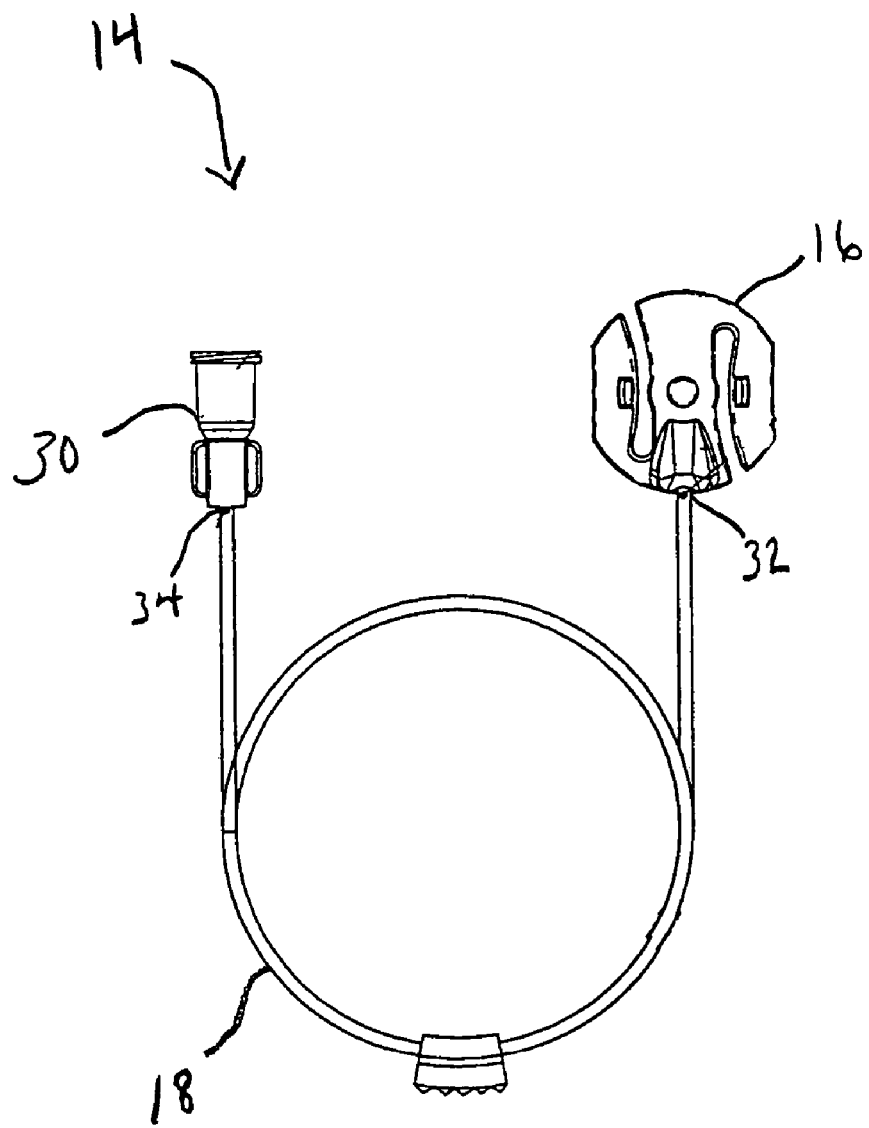
FIG. 2 shows a top view of a connector and a delivery tubing according to an embodiment of the present invention.

FIG. 2 shows a top view of the connector 16 and the delivery tubing 18 according to an embodiment of the present invention. A first end 32 of the delivery tubing 18 may be connected to the connector 16. The first end 32 of the delivery tubing 18 may be connected to the connector 16 in a permanent fashion or may be removable. Similarly, a second end 34 of the delivery tubing 18 may be connected to a fitting 30. The second end 34 of the delivery tubing 18 may be connected to the fitting 30 in a permanent fashion or may be removable.

The delivery tubing 18 may be fabricated in a variety of sizes according to embodiments of the present invention. For example, according to an embodiment of the present invention, the delivery tubing 18 may be approximately 42 inches in length. The length of the delivery tubing 18 may be determined by the user and may be any length desired by the user. In addition, the delivery tubing 18 may be made out of a variety of materials that are common in the industry for catheter-type tubings. For example, the delivery tubing 18 may be made out of TEFLON, silicone rubber, polyurethane, polyethylene, synthetic rubber, or the like.

The fitting 30 to which the second end 34 of the delivery tubing 18 may connect may be any of a variety of fittings. For example, according to embodiments of the present invention, the fitting 30 may be a male fitting or a female fitting. Also, according to embodiments of the present invention, the fitting 30 may be implemented in a variety of configurations. For example, the fitting 30 may be implemented as a Luer fitting. Alternatively, the infusion set may use a fitting as shown and described in U.S. Pat. No. 6,585,695, which is herein incorporated by reference in its entirety.

Figure 3:
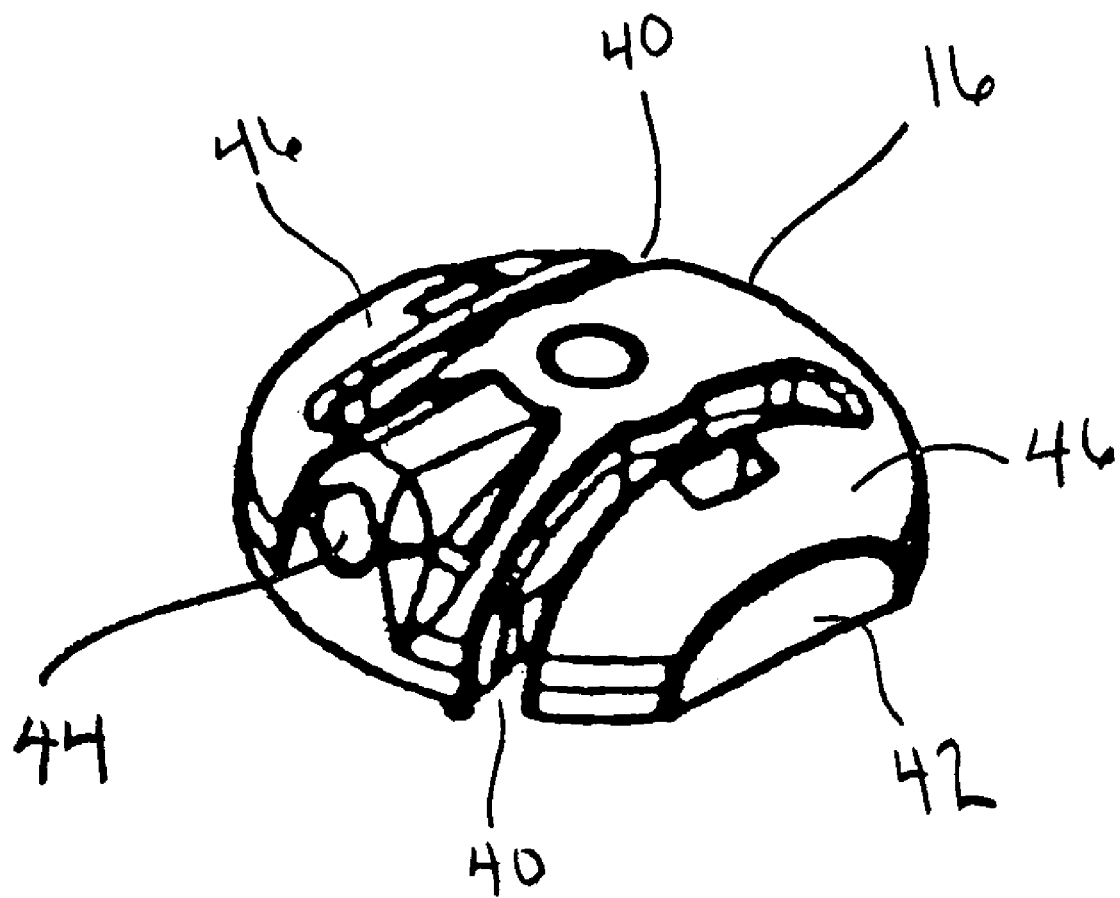
FIG. 3 shows a perspective view of a connector according to an embodiment of the present invention.

FIG. 3 shows a perspective view of the connector 16 according to an embodiment of the present invention. As can be seen in FIG. 3, the connector 16 may include, without limitation, at least one flange 46 and at least one open-ended channel 40 adjacent the flange 46. The at least one open-ended channel 40 allows the flange 46 to flex in a transverse direction, allowing the connector 16 to attach to the base 26 as will be explained greater detail below. The flange 46 may include a depression 42 which provides a region with which a patient or other user may grasp the connector 16. As can also be seen in FIG. 3, the connector 16 may include a tubing receptacle 44 into which the delivery tubing 18 may be positioned.

According to embodiments of the present invention, the connector 16 may be made from a variety of materials. For example, the connector 16 may be made from PVC, polyurethane, polyethylene, polycarbonate, plastics or the like. Also, for example, the connector 16 may be made from a transparent, semi-transparent or an opaque material.

Figure 4:
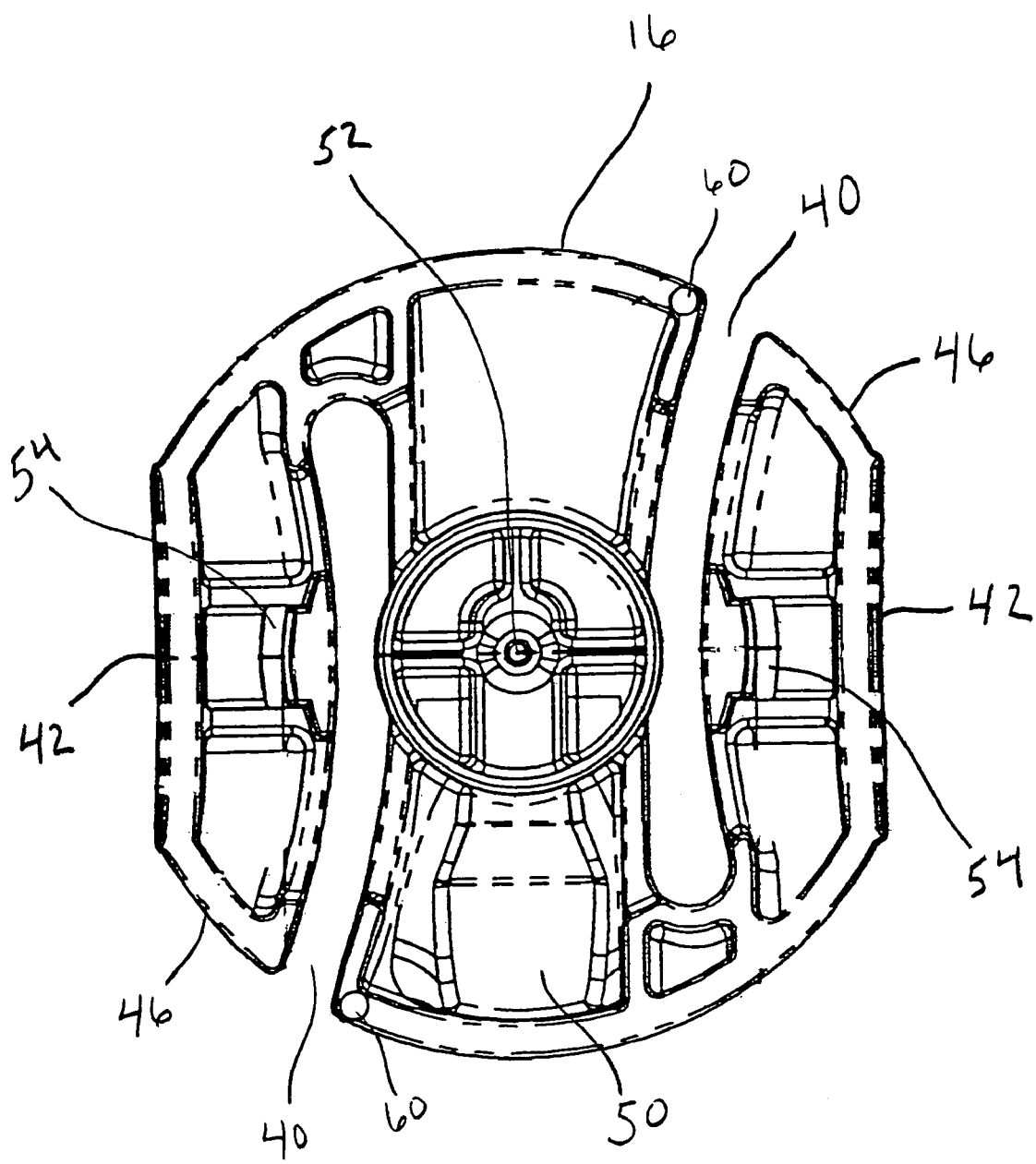
FIG. 4 shows a bottom view of a connector according to an embodiment of the present invention.

FIG. 4 shows a bottom view of the connector 16 according to an embodiment of the present invention. In the view of the connector 16 shown in FIG. 4, two open-ended channels 40 may be seen adjacent the flanges 46. In FIG. 4, the flanges 46 are formed with depressions 42. Also seen in FIG. 4, according to an embodiment of the present invention, is a chamber 50 which may be disposed adjacent the tubing receptacle 44 (not shown in FIG. 4). The chamber 50 may provide a path through which fluid moving through the delivery tubing 18 passes as it makes its way into a subcutaneous location in a patient. Also shown in FIG. 4 is a channel pin 52. According to an embodiment of the present invention shown in FIG. 4, the channel pin 52 may be disposed in a substantially perpendicular position relative to the chamber 50 and may also be coupled to the chamber 50 so as to provide a contiguous path (or passage) for fluid received from the delivery tubing 18. The channel pin 52 may also provide positioning assistance when mating the connector 16 to the base 26.

Also shown in FIG. 4 according to embodiments of the present invention are mounting hooks 54. The mounting hooks 54 may be disposed on a side of the flange 46 that interfaces with the base 26. Because the flanges 46 themselves are flexible, the mounting hooks 54 are movable with respect to the base 26 by depressing the flanges 46. Thus, the mounting hooks 54 may be positioned underneath and removed from mounting grooves on the base 26 as will be explained in greater detail below.

Also shown in FIG. 4 according to embodiments of the present invention are two stops 60. The stops 60 may be used to limit the rotation of the connector 16 in conjunction with barriers on the base 26 as will be explained in greater detail below. According to the embodiment of the present invention shown in FIG. 4, the stops 60 may be disposed on opposite sides of the connector 16. According to other embodiments of the present invention, the stops 60 may be disposed at various locations on the connector 16 and may be disposed adjacent other stops.

Figure 5:
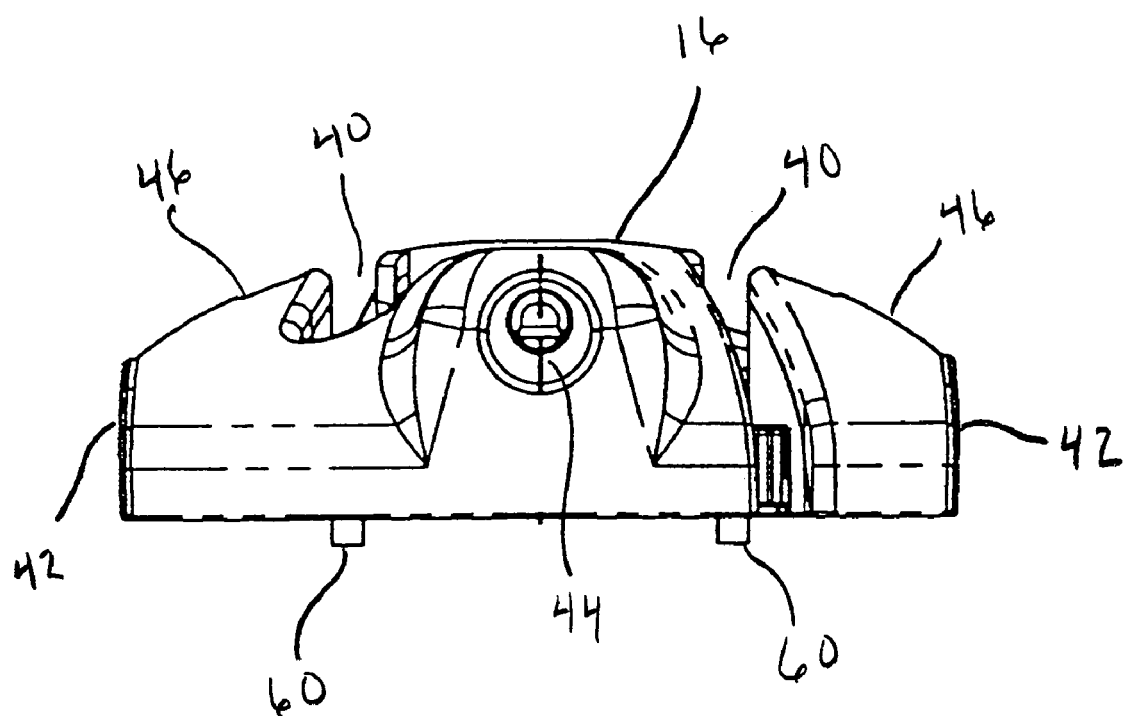
FIG. 5 shows a side view of a connector according to an embodiment of the present invention.
Figure 4:
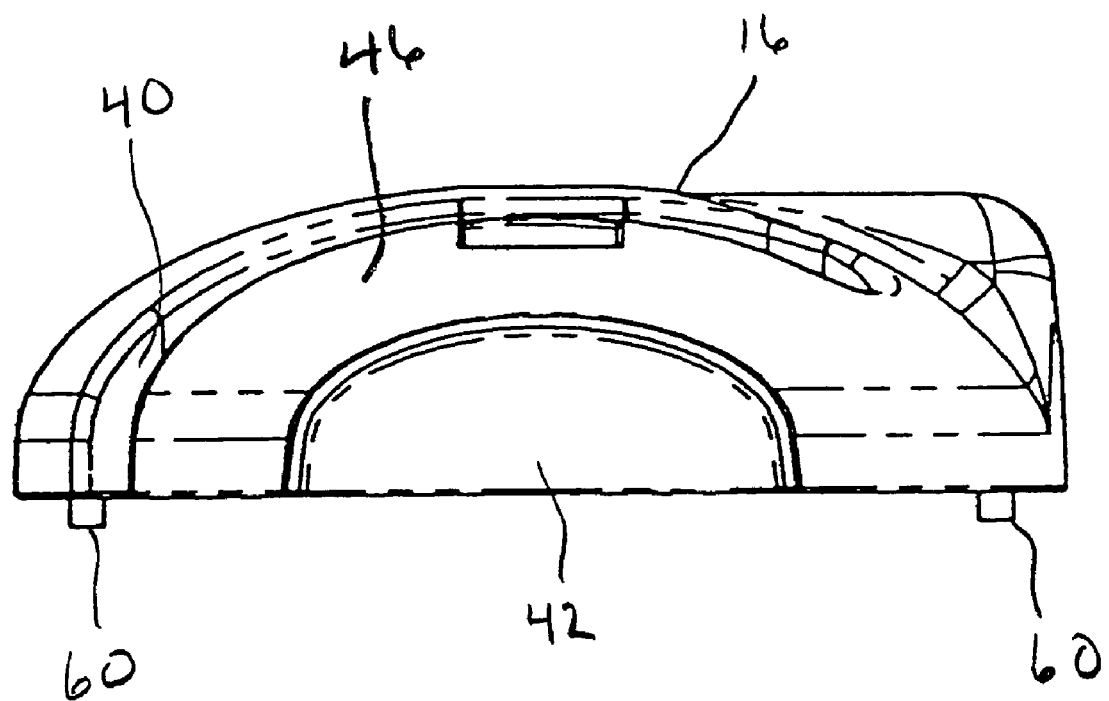

FIG. 5 shows a side view of the connector 16 according to an embodiment of the present invention. In the embodiment of the invention shown in FIG. 5, the relative locations of the open-ended channels 40, the depressions 42, the tubing receptacle 44 and the flanges 46 may be seen. Also, as shown in FIG. 5, the stops 60 may extend beyond a flat boundary of the connector 16.

FIG. 6 shows another side view of the connector 16 according to an embodiment of the present invention. In FIG. 6, the stops 60 may be seen in their relative positions at distal ends of the connector 16. According to embodiments of the present invention, the stops 60 may be disposed on a portion of the connector 16 that does not flex or flexes minimally when the flanges 46 are flexed. Thus, according to the embodiment of the invention of shown in FIG. 6, the stops 60 may remain in a relatively static position regardless of the position of the flanges 46.

Figure 7:
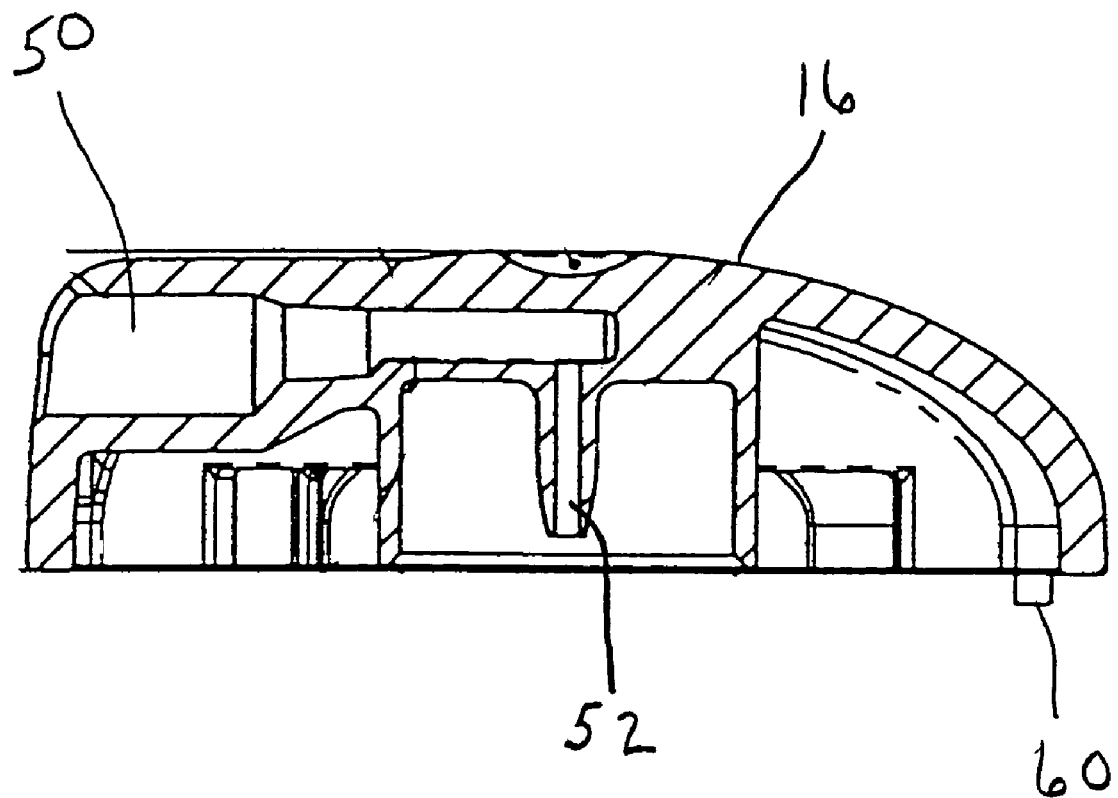
FIG. 7 shows a side cut-away view of a connector according to an embodiment of the present invention.

FIG. 7 shows a side cut-away view of the connector 16 according to an embodiment of the present invention. In FIG. 7, the chamber 50 is shown disposed in an anterior portion of the connector 16 and connecting to the channel pin 52. The channel pin 52 may be used to complete the path for fluid traveling from the delivery tubing 18 into a cannula as will be explained in greater detail below. Also seen in FIG. 7 according to an embodiment of the present invention is a stop 60 located at a distal end of the connector 16.

Figure 8:
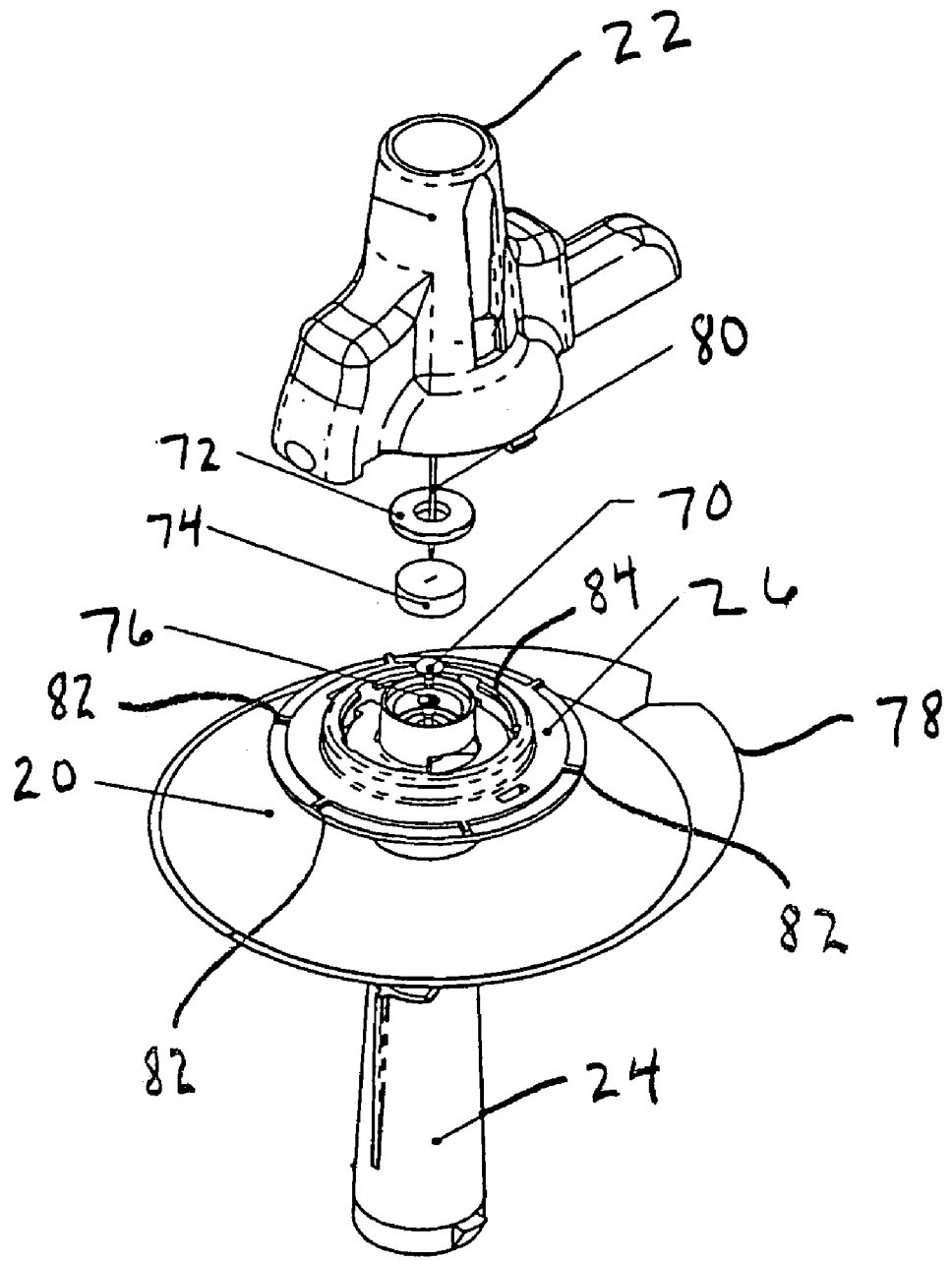
FIG. 8 shows an exploded view of a needle hub, a needle guard 24 and a base 26 according to an embodiment of the present invention.

An exploded view of the needle hub 22, the needle guard 24 and the base 26 may be seen in FIG. 8 according to an embodiment of the present invention. As can be seen in FIG. 8, a needle 80 may be attached to the needle hub 22. The needle 80 may be used to guide a cannula 76 into a subcutaneous location in a patient. The needle 80 may be made from a variety of materials. For example, the needle 80 may be made from stainless steel or any of a variety of alloys, ceramics, plastics, glasses, or the like. Also, according to an embodiment of the present invention, the needle 80 may be made in a variety of sizes from as large as 18 gauge to as small as 33 gauge (or smaller). For example, according to an embodiment of the present invention, the needle 80 may be a 28 gauge needle.

According to embodiments of the present invention, a septum 74 may be disposed in the base 26 for providing a seal. The septum 74 may be made from a resilient material and may include an opening through which the needle 80 may be inserted. According to embodiments of the present invention, a cap 72 may be positioned on top of the septum 74 for providing a retaining function for the septum 74. The needle 80 may be inserted through the septum 74 and through a needle guide 70 so that it is positioned within a lumen portion of the cannula 76. In preferred embodiments, the septum is made from a silicone rubber. However, in alternative embodiments, the septum may be formed out of other elastomeric materials, such as rubber, bromobutyl rubber, synthetic rubber, or the like.

When the needle 80 is extended through the septum 74 and into the lumen of the cannula 76, it may extend well beyond the holding pad 20. The needle guard 24 may be provided to protect a user from accidental puncture by the extended needle 80. Also, as can be seen in FIG. 8, according to an embodiment of the present invention, the holding pad 20 may be provided with adhesive protectors 78 if the holding pad 20 includes an adhesive for maintaining a position of the base 26 on a patient's skin. The adhesive protectors may be removed when the patient is ready to apply the base 26 and the holding pad 20 to the patient's skin.

The needle guard 24 may attach to the needle hub 22 to cover the needle 80 and to provide protection from accidental puncture by the needle 80. Portions of the needle guard 24 may extend through apertures in the base 26 to engage the needle hub 22. The needle guard 24 may attach to the needle hub 22 via friction fit, hooks, a locking mechanism or the like.

Also shown in FIG. 8, according to embodiments of the present invention, the base 26 may include barriers 82 and a mounting groove 84. According to embodiments of the present invention, the barriers 82 may be used in conjunction with the stops 60 on the connector 16 to limit the angular or circular movement of the connector 16 while it is attached to the base. Also according to embodiments of the present invention, the mounting groove 84 may be used in conjunction with the mounting hooks 54 for mating the connector 16 to the base 26. Thus, according to the embodiment of the invention shown in FIG. 8, the barriers 82 used in conjunction with the stops 60 on the connector 16 limit the angular or circular movement of the connector 16 while it is attached to the base while the mounting groove 84 used in conjunction with the mounting hooks 54 allow the connector 16 to mate with the base 26 in any orientation.

According to embodiments of the present invention, the base 26 may be made from a variety of materials. For example, the base 26 may be made from PVC, polyurethane, polyethylene, polycarbonate, plastics and the like. Also, for example, the base 26 may be made from a transparent, semi-transparent or an opaque material.

Figure 9:
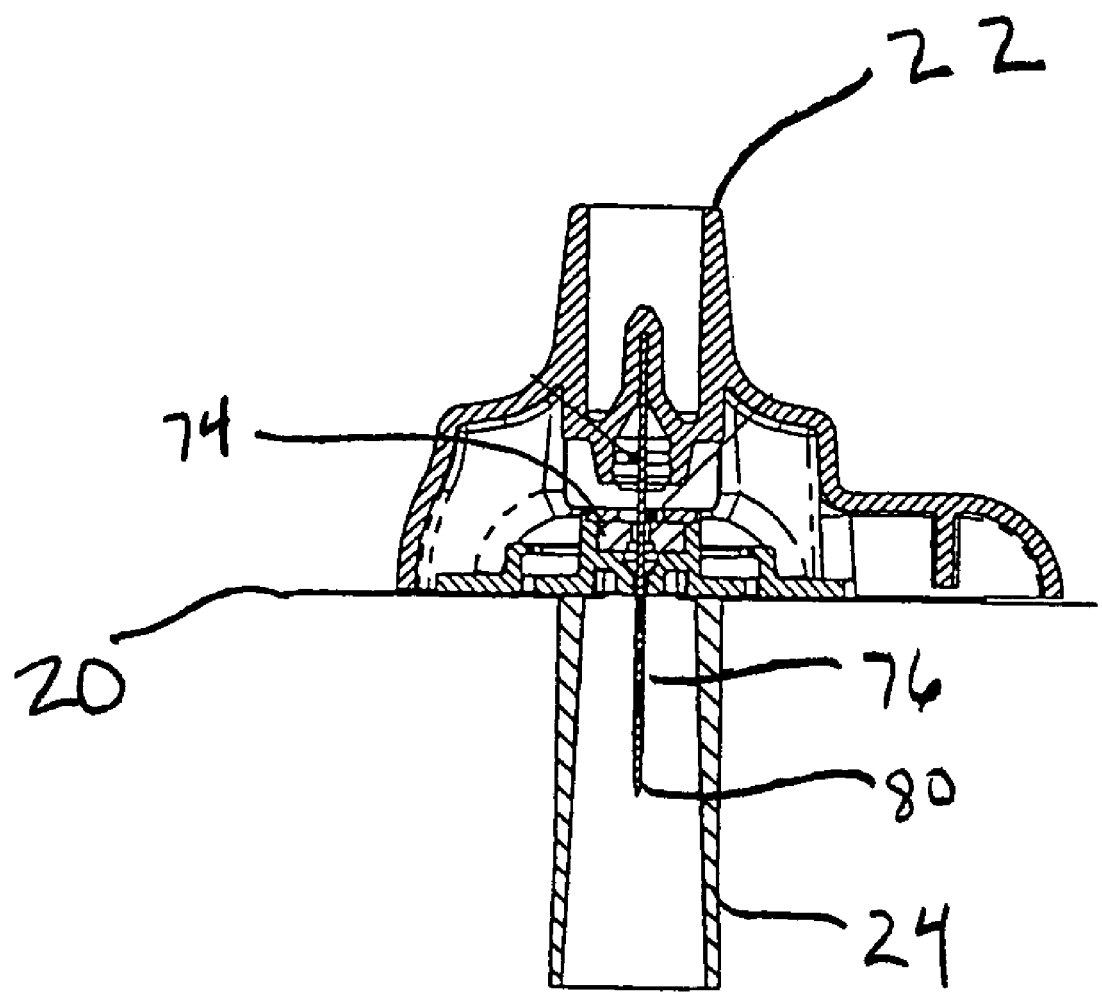
FIG. 9 shows a cut-away view of a needle hub, a needle guard and a base according to an embodiment of the present invention.

FIG. 9 shows a cut-away view of the needle hub 22, a needle guard 24 and the base 26 according to an embodiment of the present invention. As can be seen in FIG. 9, the needle 80 may extend through the septum 74, beyond the holding pad 20 and through the lumen of the cannula 76.

Figure 10:
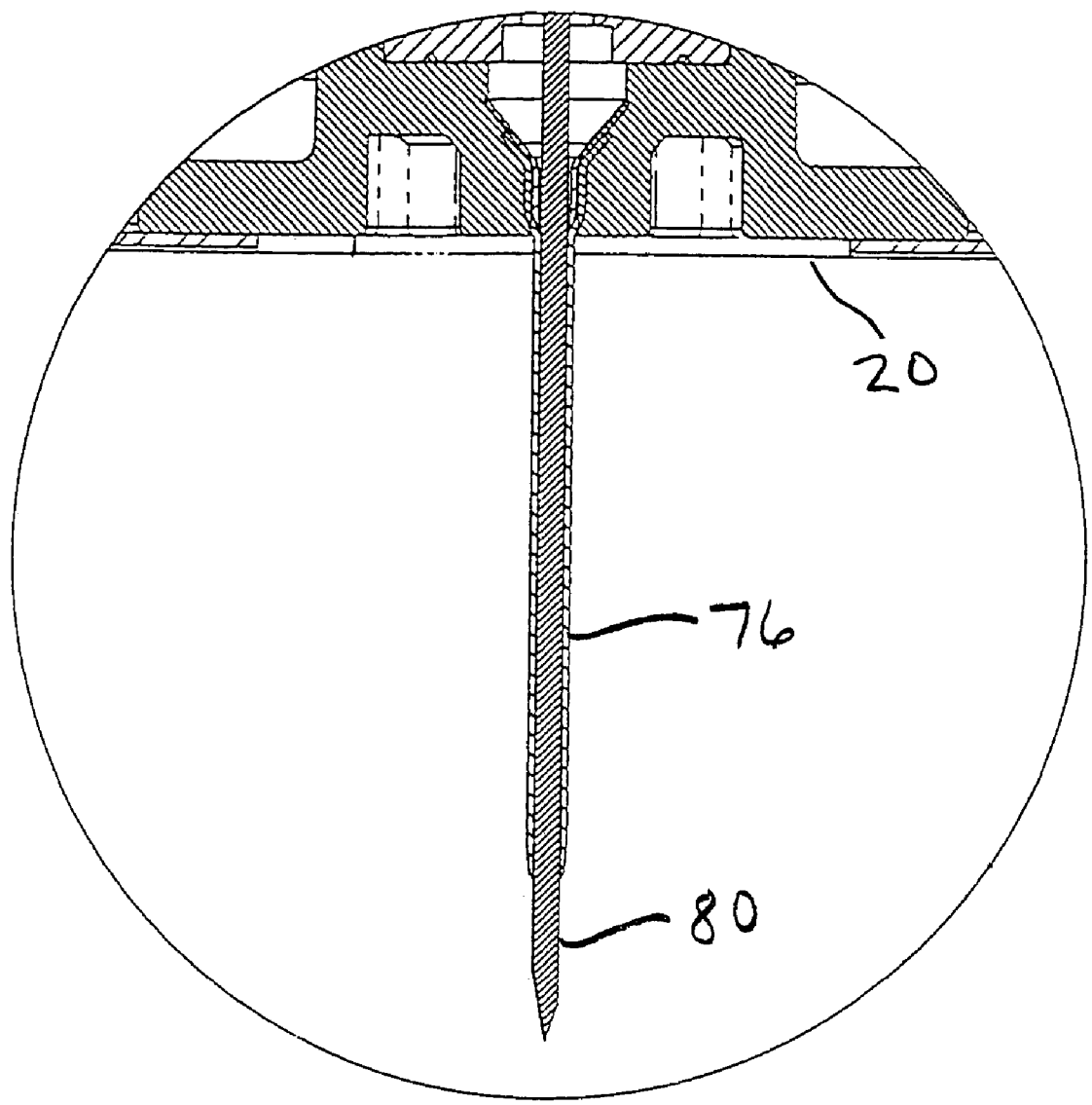
FIG. 10 shows a blown-up view of a needle and cannula portion according to an embodiment of the present invention.

FIG. 10 shows a blown-up view of the needle 80 and cannula 76 portion of FIG. 9 according to an embodiment of the present invention. In FIG. 10, the needle 80 can be seen extending past the holding pad 20 and into and through the lumen of the cannula 76. As can be seen in FIG. 10 the needle 80 may extend through the lumen of the cannula 76 and terminate in a sharp, distal end disposed at least slightly beyond a distal end of the cannula 76.

According to embodiments of the present invention, the cannula 76 may be fabricated from a soft, pliable material such as TEFLON (polytetrafluorethylene), silicone rubber, polyurethane, polyethylene, plastic, other materials coated with TEFLON or a TEFLON-like material, or the like. When the connector 16 is positioned onto the base 25, the channel pin 52 may mate with the cannula 76 to provide a contiguous path for fluid delivery from the delivery tubing 18 to a subcutaneous location in the patient.

Thus, referring to FIGS. 1, 2, 4 and 8, in operation according to an embodiment of the present invention, a patient needing an infusion of a fluid, such as a diabetic needing an infusion of insulin, for example, may remove the needle guard 24 from the needle 80, exposing the needle 80. An infusion site may be chosen by the patient and the adhesive protector 78 may be removed from the holding pad 20. The holding pad 20 may then be positioned on the skin of the patient at the chosen infusion site by inserting the needle 80 and the cannula 76 through the surface of the skin. The holding pad 20 is one example of means to positioning a base 26 on an infusion site of a user. The infusion set may be inserted into the skin by use of an insertion tool, such as that shown and described in U.S. Pat. No. 6,607,509, which is herein incorporated by reference in its entirety.

Once the needle holding pad 20 has been positioned on the skin, the needle hub 22 and the needle 80 may be removed from the base 26, leaving most of the cannula 76 at a subcutaneous position in the patient. The position of the holding pad 20 on the skin of the patient may be maintained by an adhesive on the surface of the holding pad 20 adjacent the skin.

Next the connector 16 may be positioned onto the base 26. The patient may grasp the connector 16 at the depressions 42 and apply a force at those points, thereby flexing the flanges 46 toward a center portion of the connector 16. In so doing, the mounting hooks 54, being attached to the flanges 56, will move in a similar direction. The patient may then position the connector 16 onto the base 26. Because the depressed flanges 46 and, consequently, the mounting hooks 54 will be closer to a center portion of the connector 16 than they are in their resting position, the mounting hooks 54 may fit within an interior portion of the base 26 defined by the mounting groove 84. The connector 16 may be pushed onto the base 26, thereby disposing the mounting hooks 54 at a position within an area defined by and underneath the mounting groove 84. The patient may then release the depressions 42 and the connector 16.

When the patient releases the depressions 42 and the connector 16, the flanges 46 and the mounting hooks 54 will move to their resting position. Thus, the mounting hooks will reside and be locked underneath the mounting groove 84. The flanges 46 is one example of means for positioning the connector 16 onto the base 26.

Once the connector 16 has been positioned on the base 26 in the manner just described, the patient may adjust the orientation of the connector 16 with respect to the base 26 in order to place the delivery tubing 18 at an optimum location. This may require the user to disconnect and reconnect the connector 16 to the base 26 to place the barriers 82 and stops 60 in the desired relative orientation within a selected region of allowed rotation. The orientation of the connector 16 with respect to the base 26 may be limited by the stops 60 and the barriers 82. Although the mounting hooks 54 are free to rotate about the mounting groove 84, the angular or circular movement of the connector 16 may be limited by the stops 60 and the barriers 82. The barriers 84 prevent the connector 16 from rotating freely around the base by providing physical interference to the stops 60. The disconnection and reconnection of the connector 16, and the rotation of the connector 16 provide two examples of means for adjusting the position of the delivery tubing 18 for the user.

Thus, for example, according to an embodiment of the present invention, if the barriers 84 are spaced around a circumference of the base 26 at 60 degree intervals, the angular or circular movement of the connector 16 around the base 26 will be limited to 60 degrees. According to other embodiments of the present invention, the barriers 84 may be spaced around a circumference of the base 26 at a variety of intervals. For example, if the barriers 84 are spaced around a circumference of the base 26 at 90 degree intervals, the angular or circular movement of the connector 16 around the base 26 will be limited to 90 degrees. In preferred embodiments, there is at least one stop 60 and barrier 82 so that the rotation is limited to less than 360 degrees. However, in alternative embodiments, more stops and barriers may be used to limit rotation to, including but not limited to, 180 degrees, 120 degrees, 90 degrees, 75 degrees, 60 degrees, 45 degrees, 30 degrees, 15 degrees, or the like. In preferred embodiments, the minimum rotation is 1 degree or larger, such as but not limited to, 2 degrees, 5 degrees, 7.5 degrees, 10 degrees or the like. Theoretically, the stops and barriers could be positioned so that the connector 16 can be coupled to the base 26 with very little rotational movement. In a further alternative embodiment, the stops and barriers are shaped and configured to allow placement of the connector 16 in any orientation on the base 26 without rotational movement upon completion of the connection. Thus, in this embodiment the user can place the connection at any angle and have no relative movement once the connector 26 is locked to the base 26.

Once the connector 16 has been oriented on the base 26 in a desired position, the fitting 30 may be attached to an infusion pump or other drug or fluid delivery system and infusion of a drug or fluid into the patient at the chosen subcutaneous location may commence.

Thus, advantages of embodiments of the present invention may be readily apparent. The connector 16 is not bound to a single position on the base 26. If the delivery tubing 18 is not oriented in a desired or optimum position when the connector 16 is positioned on the base, the patient may rotate the connector 16 until the delivery tubing 18 is positioned at a desired orientation. At the same time, because the barriers 84 and the stops 60 limit the angular or circular movement of the connector 16, the delivery tubing 18 avoids entanglement, twisting and kinking that may be associated with infusion sets having connectors whose rotational movement is not restricted.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. An infusion set, comprising:
   a base for providing a subcutaneous infusion path in a first generally linear direction, said base having a first surface that faces a skin surface of a user when said base is supported on said skin surface and when said infusion set is used to pass fluids to said user;
   a cannula connected to and extending away from the base;
   a connector removably attachable to the base, the connector having a fluid flow path that extends in generally the first linear direction and aligns with the linear subcutaneous path upon the connector being attached to the base; and
   a tubing affixed to the connector,
   wherein the connector is rotatable on the base more than 5 degrees while the cannula is at a subcutaneous position and limited to less than 360 degrees around an axis that is substantially perpendicular to said first surface of said base, when the connector is removably attached to the base,
   wherein the connector comprises at least one stop surface for inhibiting rotation of the connector beyond 360 degrees; and
   wherein a contiguous passage for passing fluids is formed from the tubing to the cannula when the connector is removably attached to the base.

2. The infusion set of claim 1, wherein the base comprises at least one barrier extending away from a surface of the base.

3. The infusion set of claim 2, wherein the at least one stop surface extends away from a surface of the connector.

4. The infusion set of claim 3, wherein the at least one barrier is disposed on the base so that it restricts the movement of the at least one stop surface when the connector is rotated about the base.

5. The infusion set of claim 1, wherein the connector is limited to a rotation of 60 degrees when the connector is removably attached to the base.

6. The infusion set of claim 1, wherein the connector is limited to a rotation of 90 degrees when the connector is removably attached to the base.

7. The infusion set of claim 1, wherein the connector is limited to a rotation of 120 degrees when the connector is removably attached to the base.

8. The infusion set of claim 1, further comprising:
a hub removably affixable to the base;
a needle attached to the hub, the needle being removably insertable into the cannula; and
a cover for covering the needle.

9. The infusion set of claim 8, further comprising an adhesive pad affixed to the base, wherein the cannula extends through the adhesive pad.

10. The infusion set of claim 1, wherein the connector is rotatable on the base to more than 10 degrees and limited to less than 360 degrees around said axis.

11. The infusion set of claim 1, wherein said base comprises at least two barriers that are spaced apart from each other around a circumference of said base to create at least two rotational intervals around the circumference of said base for the rotation of the connector.

12. The infusion set of claim 1,
wherein the connector has a port, the tubing affixed to the port of the connector; and
wherein the connector comprises a single, unitary body in which the fluid flow path is contiguous with the port for providing a fluid flow connection between the port and the fluid flow path extending in generally the first linear direction.

13. A method for using an infusion set, comprising:
positioning a base on an infusion site of a user, said base having a first surface that faces a skin surface of said user when said base is supported on said skin surface and positioned on said infusion site, the base for providing a subcutaneous infusion path in a first generally linear direction;
positioning a connector onto the base, the connector comprising a delivery tubing and at least one stop surface for inhibiting rotation of the connector beyond 360 degrees with respect to the base, the connector having a fluid flow path that extends in generally the first linear direction and aligns with the linear subcutaneous path upon the connector being positioned on the base; and
adjusting a position of the delivery tubing, to rotate more than 5 degrees while a cannula is at a subcutaneous position and the rotation is limited to less than 360 degrees in a rotational direction around an axis that is substantially perpendicular to said first surface of said base.

14. The method of claim 13, wherein adjusting the position of the delivery tubing is limited to a range of 120 degrees.

15. The method of claim 13, wherein adjusting the position of the delivery tubing is limited to a range of 90 degrees.

16. The method of claim 13, wherein adjusting the position of the delivery tubing is limited to a range of 60 degrees.

17. The method of claim 13, wherein adjusting the position of the delivery tubing is limited to a range of 30 degrees.

18. The method of claim 13, wherein said adjusting the position of the delivery tubing is allowed to more than 10 degrees and limited to less than 360 degrees in said rotational direction around said axis.

19. The method of claim 13, wherein said base comprises at least two barriers that are spaced apart from each other around a circumference of said base to create at least two rotational intervals around the circumference of said base for the rotation of the connector.

20. The method of claim 13,
wherein the connector has a port, the tubing affixed to the port of the connector; and
wherein the connector comprises a single, unitary body in which the fluid flow path is contiguous with the port for providing a fluid flow connection between the port and the fluid flow path extending in generally the first linear direction.

21. A subcutaneous infusion set, comprising:
a base portion having a receiving area, said base portion having a first surface that faces a skin surface of a user when said base portion is supported on said skin surface and when said subcutaneous infusion set is used to pass fluids to said user, the base portion for providing a subcutaneous infusion path in a first generally linear direction;
a cannula affixed to the base portion;
a connector portion for removable attachment to the base, the connector portion being received in the receiving area of the base portion, the connector portion having a fluid flow path that extends in generally the first linear direction and aligns with the linear subcutaneous path upon the connector portion being attached to the base portion; and
a tubing affixed to the connector portion,
wherein an angular movement of the connector portion is allowed to be more than 5 degrees while the cannula is at a subcutaneous position and is restricted by the base portion to less than 360 degrees around an axis that is substantially perpendicular to said first surface of said base portion,
wherein the connector portion comprises at least one stop surface for inhibiting rotation of the connector beyond 360 degrees, and
wherein a fluid passes from the tubing to the cannula when the connector portion is attached to the base.

22. The infusion set of claim 21, wherein the base portion comprises at least one first member extending away from a surface of the base portion.

23. The infusion set of claim 22, wherein the at least one stop surface extends away from a surface of the connector portion.

24. The infusion set of claim 23, wherein the at least one first member is disposed on the base portion so that it restricts the movement of the at least one stop surface when the connector portion is rotated about the base portion.

25. The infusion set of claim 21, wherein the connector portion is limited to a rotation of 60 degrees when the connector portion is removably attached to the base portion.

26. The infusion set of claim 21, wherein the connector portion is limited to a rotation of 90 degrees when the connector portion is removably attached to the base portion.

27. The infusion set of claim 21, wherein the connector portion is limited to a rotation of 120 degrees when the connector portion is removably attached to the base portion.

28. The infusion set of claim 21, further comprising:
a hub removably affixable to the base portion;
a needle attached to the hub, the needle being removably insertable into the cannula; and
a cover for covering the needle.

29. The infusion set of claim 28, further comprising an adhesive pad affixed to the base, wherein the cannula extends through the adhesive pad.

30. The infusion set of claim 21, wherein the angular movement of the connector portion is further allowed to more than 10 degrees around said axis.

31. The infusion set of claim 21, wherein said base comprises at least two barriers that are spaced apart from each other around a circumference of said base to create at least two rotational intervals around the circumference of said base for the rotation of the connector.

32. The infusion set of claim 21,
wherein the connector portion has a port, the tubing affixed to the port of the connector portion; and
wherein the connector portion comprises a single, unitary body in which the fluid flow path is contiguous with the port for providing a fluid flow connection between the port and the fluid flow path extending in generally the first linear direction.

33. An infusion set, comprising:
a base for providing a subcutaneous infusion path in a first generally linear direction;
a cannula connected to and extending away from the base;
a connector removably attachable to the base in any one of at least two different connection positions, said connector being rotatable more than 5 degrees on said base while the cannula is at a subcutaneous position, each connection position of said at least two different connection positions allowing for different possible relative orientations of said connector with respect to said base when said connector is rotated on said base, the connector having a fluid flow path that extends in generally the first linear direction and aligns with the linear subcutaneous path upon the connector being attached to the base; and
a tubing affixed to the connector,
wherein said base comprises at least two barriers that are spaced apart from each other around a circumference of said base;
wherein said connector comprises a stop surface for preventing further rotation of said connector in a particular rotational direction on said base when said stop surface contacts one of said at least two barriers of said base; and
wherein a plurality of intervals around said circumference of said base are defined between barriers of said at least two barriers; and
wherein each of the at least two different connection positions provides for placing the stop surface of the connector within a respectively different interval of said plurality of intervals than all other connection positions of said at least two different connection positions.

34. The infusion set of claim 33,
wherein a first interval of said plurality of intervals is limited to less than 120 degrees around said circumference of said base.

35. The infusion set of claim 33,
wherein said connector includes a plurality of stops, each stop of said plurality of stops being located in a respectively different interval of said plurality of intervals when said connector is attached to said base.

36. The infusion set of claim 33,
wherein the connector has a port, the tubing affixed to the port of the connector; and
wherein the connector comprises a single, unitary body in which the fluid flow path is contiguous with the port for providing a fluid flow connection between the port and the fluid flow path extending in generally the first linear direction.

37. An infusion set comprising:
a base for providing a subcutaneous infusion path in a first generally linear direction;
a cannula connected to and extending away from the base;
a connector removably attachable to the base in any one of at least two different connection positions, said connector being rotatable more than 5 degrees on said base while the cannula is at a subcutaneous position, each connection position of said at least two different connection positions allowing for different possible relative orientations of said connector with respect to said base when said connector is rotated on said base, the connector having a fluid flow path that extends in generally the first linear direction and aligns with the linear subcutaneous path upon the connector being attached to the base; and
a tubing affixed to the connector;
wherein the connector comprises at least one stop surface for inhibiting rotation of the connector beyond 360 degrees;
wherein said base comprises at least two barriers that are spaced apart from each other around a circumference of said base;
wherein said at least one stop surface contacts one of said at least two barriers of said base;
wherein a plurality of intervals around said circumference of said base are defined between barriers of said at least two barriers; and
wherein each of the at least two different connection positions provides for placing the stop of the connector within a respectively different interval of said plurality of intervals than all other connection positions of said at least two different connection positions.

38. The infusion set of claim 37,
wherein a first interval of said plurality of intervals is limited to less than 120 degrees around said circumference of said base.

39. The infusion set of claim 37,
wherein said connector includes a plurality of stops, each stop of said plurality of stops being located in a respectively different interval of said plurality of intervals when said connector is attached to said base.

40. The infusion set of claim 37,
wherein the connector has a port, the tubing affixed to the port of the connector; and
wherein to connector comprises a single, unitary body in which to fluid flow path is contiguous with the port for providing a fluid flow connection between the port and the fluid flow path extending in generally to first linear direction.

* * * * *